United States Patent
Muramatsu

(10) Patent No.: US 11,243,544 B2
(45) Date of Patent: Feb. 8, 2022

(54) OCCUPANT ASSIST APPARATUS

(71) Applicant: TOYOTA JIDOSHA KABUSHIKI KAISHA, Toyota (JP)

(72) Inventor: Junya Muramatsu, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 90 days.

(21) Appl. No.: 16/569,730

(22) Filed: Sep. 13, 2019

(65) Prior Publication Data

US 2020/0097018 A1 Mar. 26, 2020

(30) Foreign Application Priority Data

Sep. 20, 2018 (JP) .............................. JP2018-175698

(51) Int. Cl.
*G05D 1/00* (2006.01)
*G05D 1/02* (2020.01)
(Continued)

(52) U.S. Cl.
CPC ......... *G05D 1/0225* (2013.01); *A61B 5/0261* (2013.01); *A61B 5/1118* (2013.01); *A61B 5/1176* (2013.01); *A61B 5/391* (2021.01); *A61B 5/4519* (2013.01); *A61B 5/4803* (2013.01); *A61B 8/08* (2013.01); *A61H 39/04* (2013.01);
(Continued)

(58) Field of Classification Search
CPC ............... G05D 1/0225; G05D 1/0088; G05D 2201/0213; G01C 21/36; G01C 21/3484; G01C 21/3415; G01C 21/3461; G01C 21/343; A61B 5/391; A61B 5/1118; A61B 5/4519; A61B 5/0261; A61B 5/1176; A61B 5/4803; A61B 8/08; A61B 5/6893; A61B 5/204; A61H 39/04

See application file for complete search history.

(56) References Cited

U.S. PATENT DOCUMENTS

2017/0123423 A1* 5/2017 Sako .................... G05D 1/0088

FOREIGN PATENT DOCUMENTS

JP 2005-050202 A 2/2005
JP 2005-087543 A 4/2005
(Continued)

OTHER PUBLICATIONS

Mayton, A., and Wible, D., "Preventing Exposure To Whole-Body Vibration", Pit & Quarry, Jan. 2019, pp. 72-76 [retrieved on Aug. 27, 2021], Retrieved from the Internet:< URL: https://www.cdc.gov/niosh/mining/UserFiles/works/pdfs/petwb.pdf>. (Year: 2019).*

(Continued)

*Primary Examiner* — Peter D Nolan
*Assistant Examiner* — Peter Y Ning
(74) *Attorney, Agent, or Firm* — Oliff PLC

(57) ABSTRACT

An occupant assist apparatus (12) has: a receiving device (121) for receiving an occupant information relating to an occupant of a vehicle; an estimating device (122) for estimating, on the basis of the occupant information, at least one of a desire of the occupant to urinate and a desire of the occupant to defecate in a future than a timing when the occupant information is received; and an executing device (123) for executing an occupant assist on the basis of a result of an estimation by the estimating device.

7 Claims, 4 Drawing Sheets

(51) Int. Cl.
  *G01C 21/36* (2006.01)
  *G01C 21/34* (2006.01)
  *A61B 5/11* (2006.01)
  *A61B 5/00* (2006.01)
  *A61B 5/026* (2006.01)
  *A61B 5/1171* (2016.01)
  *A61H 39/04* (2006.01)
  *A61B 8/08* (2006.01)
  *A61B 5/391* (2021.01)

(52) U.S. Cl.
  CPC ..... *G01C 21/3415* (2013.01); *G01C 21/3484* (2013.01); *G01C 21/36* (2013.01); *G05D 1/0088* (2013.01); *G05D 2201/0213* (2013.01)

(56) References Cited

FOREIGN PATENT DOCUMENTS

| JP | 2009198216 A | * | 9/2009 |
| JP | 2013-153820 A | | 8/2013 |
| JP | 2013153820 A | * | 8/2013 |
| JP | 2016-137203 A | | 8/2016 |
| JP | 2016-215751 A | | 12/2016 |
| JP | 2018-055691 A | | 4/2018 |
| KR | 10-2014-0044036 A | | 4/2014 |

OTHER PUBLICATIONS

It was Attacked by Uresiesthesia During Traffic Congestion of U-turn! Secret Technique of People without Portable Toilet is Colet—J-CAST News, https://www.j-cast.com/2016/08/15275274.html?p=a11, Aug. 15, 2016.
Kurashiki, "Super-special points" Teaching books, Okayama News on Medical health guides on Okayama, https://www.medica.sanyonews.jp/article/3881, pp. 2014 to 08 and 19, retrieved on Nov. 21, 2021.
A method of cutting off a pinch by pushing the same into a ESSEonline, 2017, https://esse-online.jp/articles/-/11770, retrieved on Nov. 30, 2021.

* cited by examiner

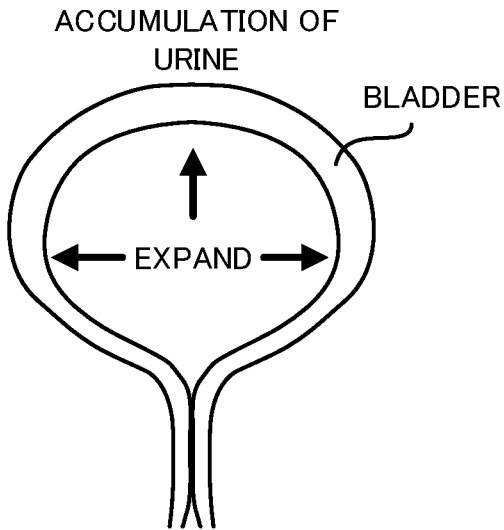 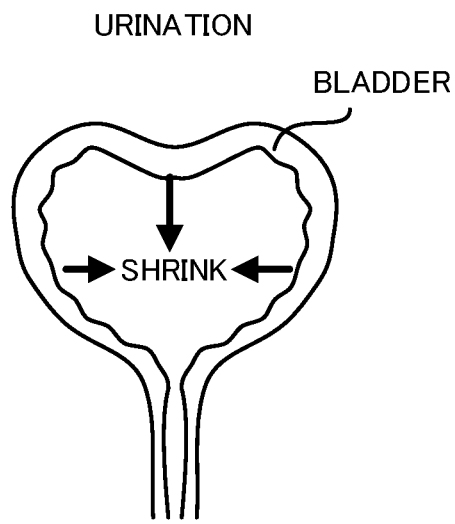
FIG. 3A  FIG. 3B
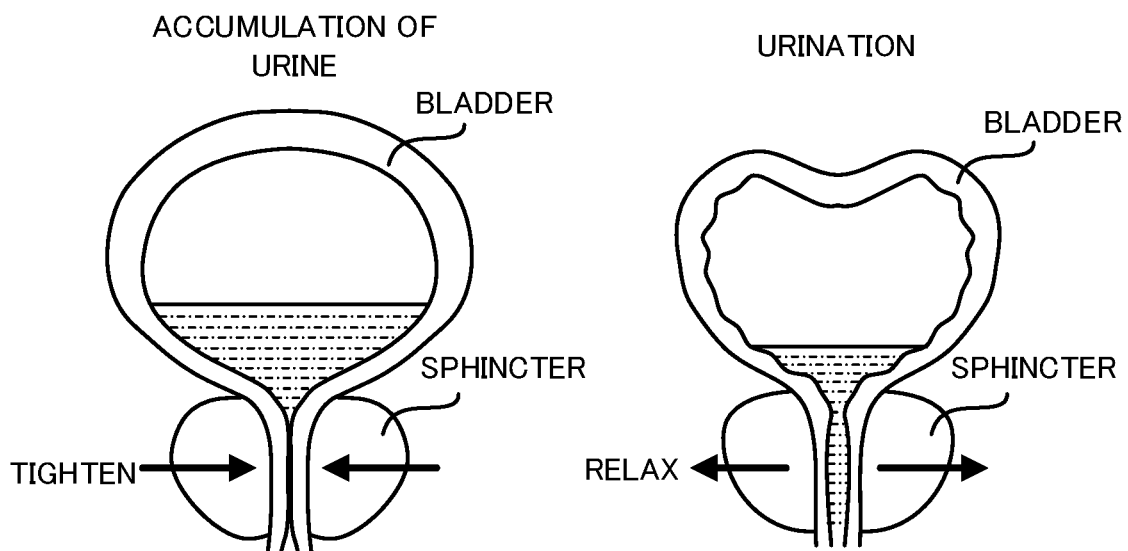
FIG. 4A  FIG. 4B

OCCUPANT ASSIST APPARATUS

TECHNICAL FIELD

The present invention relates to a technical field of an occupant assist apparatus that is configured to estimate at least one of a desire of an occupant to urinate and a desire of the occupant to defecate and to execute an occupant assist based on the estimated result, for example.

BACKGROUND ART

A Patent Literature 1 discloses an autonomous vehicle that is configured to change a vehicle mode on the basis of a result of determining at least one of a desire of an occupant of the vehicle to urinate and a desire of the occupant to defecate. Specifically, the Patent Literature 1 discloses the autonomous vehicle that is configured to determine a condition of the desire of the occupant to urinate and the desire of the occupant to defecate on the basis of both of a result of recognizing a captured image of the occupant and a voice of the occupant and to change the vehicle mode to a forced autonomous driving mode by which a destination is set to the nearest place having a restroom (i.e. a toilet) when it is determined that the occupant feels the desire to urinate or defecate.

There is a Patent Literature 2 as another document relating to the present invention. The Patent Literature 2 discloses an excretion predicting apparatus that is configured to predict an excretion of a target person on the basis of a stage of a sleeping of the sleeping target person who is cared in a care house.

CITATION LIST

Patent Literature

[Patent Literature 1] Japanese Unexamined Patent Application Publication No. 2018-055691
[Patent Literature 2] Japanese Unexamined Patent Application Publication No. 2013-153820

SUMMARY OF INVENTION

Technical Problem

The autonomous vehicle disclosed in the Patent Literature 1 determines that the occupant feels the desire to urinate or defecate when the captured image of the occupant shows that the occupant squirms and the occupant utters a voice of "the restroom (the toilet)" or "I almost pee my pants". Namely, the autonomous vehicle disclosed in the Patent Literature 1 changes the vehicle mode on condition that the occupant already feels the desire to urinate or defecate at the timing of the determination (namely, now). The autonomous vehicle disclosed in the Patent Literature 1 has a room for improvement in changing the vehicle mode more appropriately.

Moreover, not only the autonomous vehicle that is configured to change the vehicle mode on the basis of the result of determining at least one of the desire of the occupant to urinate and the desire of the occupant to defecate but also an occupant assist apparatus that is configured to execute any occupant assist on condition that the occupant already feels the desire to urinate or to defecate now has a room for improvement in executing the occupant assist more appropriately.

The above described technical problem is one example of the technical problem to be solved by the present invention. It is therefore an object of the present invention to provide, for example, an occupant assist apparatus that is configured to estimate at least one of a desire of an occupant to urinate and a desire of the occupant to defecate and to execute an occupant assist based on the estimated result more appropriately.

Solution to Problem

One aspect of an occupant assist apparatus of the present invention has: a receiving device that is configured to receive an occupant information relating to an occupant of a vehicle; an estimating device that is configured to estimate, on the basis of the occupant information, at least one of a desire of the occupant to urinate and a desire of the occupant to defecate in a future than a timing when the occupant information is received; and an executing device that is configured to execute an occupant assist on the basis of a result of an estimation by the estimating device.

BRIEF DESCRIPTION OF DRAWINGS

FIG. 3 Each of FIG. 3A
and FIG. 3B is a cross-sectional view that illustrates a condition of a bladder.
FIG. 4 Each of FIG. 4A
and FIG. 4B is a cross-sectional view that illustrates a condition of a urinary sphincter.

DESCRIPTION OF EMBODIMENTS

Hereinafter, with reference to drawings, one embodiment of the occupant assist apparatus of the present invention will be described. In the following description, a vehicle 1 to which one embodiment of the occupant assist apparatus of the present invention is adapted will be described.

(1) Structure of Vehicle 1

Figure 1:
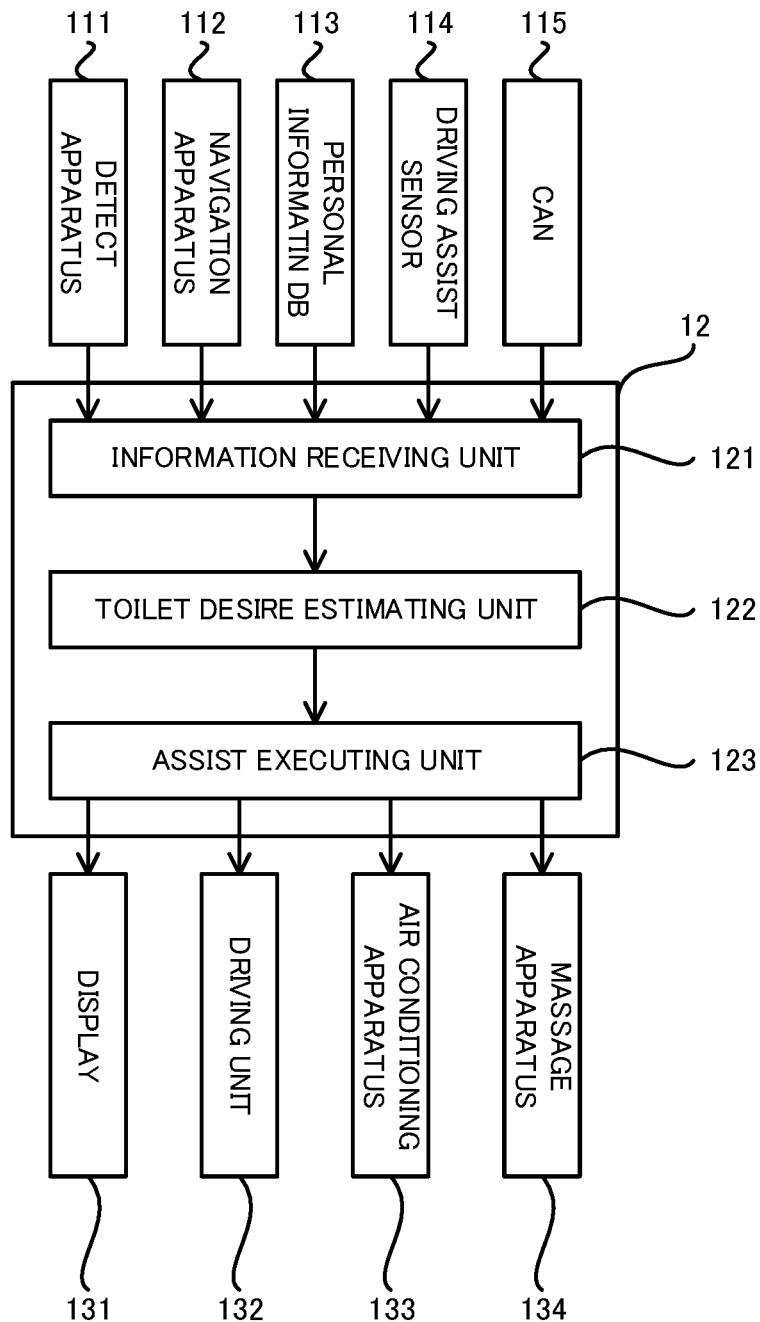
FIG. 1 is a block diagram that illustrates a structure of a vehicle in a present embodiment.

Firstly, with reference to FIG. 1, a structure of the vehicle 1 in the present embodiment will be explained. FIG. 1 is a block diagram that illustrates the structure of the vehicle 1 in a present embodiment.

As illustrated in FIG. 1, the vehicle 1 has: a detect apparatus 111; a navigation apparatus 112; a personal information DB (DataBase) 113; a driving assist sensor 114; a CAN (Control Area Network) 115; an EU (Electronic Control Unit) 12 that is one example of an "occupant assist apparatus" or a "controller" in a below described additional statement, a display 131, a driving unit 132; an air conditioning apparatus 133; and a massage apparatus 134.

The detect apparatus 111 is a detect apparatus that is configured to detect an occupant information relating to an occupant (for example, at least one of a driver and a passenger) of the vehicle 1. Especially in the present embodiment, the detect apparatus 111 is configured to detect the occupant information that has some relation with at least one of a desire of the occupant to urinate and a desire of the occupant to defecate. A biological information of the occupant is one specific example of the occupant information that is detectable by the detect apparatus 111. Note that the biological information in the present embodiment includes not only an information relating to a vital sign of the occupant but also any information that varies depending on a condition of the occupant and a variation of which is detectable by using a method of some kind. A detected result of the detect apparatus 111 (namely, the occupant information) is outputted to the ECU 12.

The navigation apparatus 112 is configured to execute a navigation operation to the vehicle 1. Especially in the present embodiment, the navigation apparatus 112 is configured to output, to the ECU 12, the occupant information (especially, the occupant information that has some relation with at least one of the desire of the occupant to urinate and the desire of the occupant to defecate) that is unique to the navigation operation.

The personal information DB 113 is an apparatus that is configured to store a personal information of the occupant that is one specific example of the occupant information. Especially, the personal information DB 113 is configured to store the personal information that has some relation with at least one of the desire of the occupant to urinate and the desire of the occupant to defecate. The personal information may be inputted to the personal information DB 113 via an information terminal (for example, a smart phone and the like) by the occupant. The personal information may be inputted to the personal information DB 113 via an apparatus that is configured to receive (in other words, collect) the personal information (for example, a smart phone having a sensor and/or an application for receiving (in other words, collecting) the personal information and the like) without the input from the occupant. The occupant information stored in the personal information DB 113 (namely, the personal information) is outputted to the ECU 12. Note that the vehicle 1 may not have the personal information DB 113 necessarily. In this case, the persona information may be transmitted to the ECU 12 from the personal information DB 113 that is placed outside of the vehicle 1 (for example, the personal information DB 113 that is placed in a mobile terminal of the occupant or an external server)

The driving assist sensor 114 is an apparatus that is configured to detect a condition (in other words, a behavior) of the vehicle 1 that is driven by the occupant. It can be said that an information relating to the condition of the vehicle 1 is one specific example of the occupant information, because the condition of the vehicle 1 results from the driving by the occupant. Especially, the driving assist sensor 114 is configured to detect the condition of the vehicle 1 (namely, the occupant information) hat has some relation with at least one of the desire of the occupant to urinate and the desire of the occupant to defecate. At least one of a brake frequency, an acceleration condition of the vehicle 1 and an inter-vehicular distance is one example of this condition of the vehicle 1. In this case, the driving assist sensor 114 may include at least one of a brake pedal sensor, a speed sensor, a millimeter-wave radar, an ultrasonic sensor and a camera (for example, a vehicle exterior monitoring camera), for example. A detected result of the driving assist sensor 114 (namely, the occupant information) is outputted to the ECU 12.

The CAN 115 is a network through which the information relating to the condition of the vehicle 1 is transmitted. The ECU 12 receives the occupant information (for example, the occupant information relating to the condition of the vehicle 1 that has some relation with at least one of the desire of the occupant to urinate and the desire of the occupant to defecate) via the CAN 115.

The ECU 12 is configured to control entire operation of the vehicle 1. Especially in the present embodiment, the ECU 12 is configured to estimate at least one of the desire of the occupant to urinate and the desire of the occupant to defecate and to execute an assist operation for executing an occupant assist based on an estimated result. In order to execute the assist operation, the ECU 12 includes, as processing blocks that are logically realized in the ECU 12, an information receiving unit 121 that is one example of a "receiving device" in the below described additional statement, a toilet desire estimating unit 122 that is one example of an "estimating device" in the below described additional statement and an assist executing unit 123 that is one example of an "executing device" in the below described additional statement. Although the operation of each of the information receiving unit 121, the toilet desire estimating unit 122 and the assist executing unit 123 will be described later in detail with reference to the FIG. 2 and so on, it is briefly described here. The information receiving unit 121 is configured to receive the occupant information from the detect apparatus 111, the navigation apparatus 112, the personal information DB 113, the driving assist sensor 114 and the CAN 115. The toilet desire estimating unit 122 is configured to estimate at least one of the desire of the occupant to urinate and the desire of the occupant to defecate on the basis of the occupant information received by the information receiving unit 121. The assist executing unit 123 is configured to determine a content of the occupant assist that is provided to the occupant on the basis of an estimated result of the toilet desire estimating unit 122 and to execute the occupant assist having the determined content.

The display 131 is an apparatus that is configured to display a desired information. The display 131 may be a display of the navigation apparatus 112. The driving unit 132 is a unit of apparatuses of the vehicle 1 used for driving the vehicle 1. The driving unit 132 includes at least one of a power source of the vehicle 1 (for example, at least one of an engine and a motor), a brake apparatus of the vehicle 1 and a steering apparatus of the vehicle 1, for example. The air conditioning apparatus 133 is an apparatus that is configured to control a temperature in a vehicle cabin of the vehicle 1. The massage apparatus 134 is an apparatus that is configured to massage the occupant. Each of the display 131, the driving unit 132, the air conditioning apparatus 133 and the massage apparatus 134 is used for executing the occupant assist.

(2) Flow of Assist Operation

Figure 2:
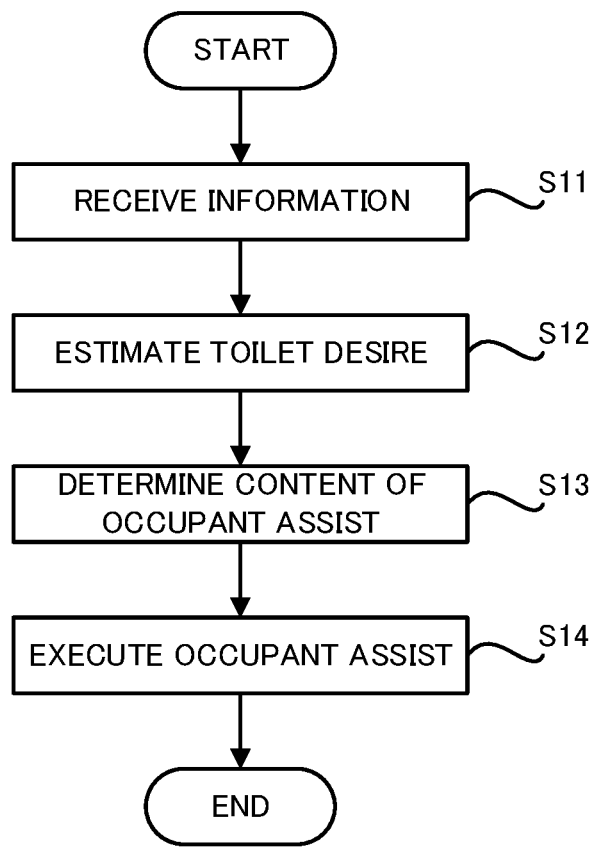
FIG. 2 is a flowchart that illustrates a flow of an assist operation in the present embodiment.

Next, with reference to FIG. 2, a flow of the assist operation executed by the ECU 12 will be described. FIG. 2 is a flowchart that illustrates the flow of the assist operation in the present embodiment.

As illustrated in FIG. 2, the information receiving unit 121 receives the occupant information from each of the detect apparatus 111, the navigation apparatus 112, the personal information DB 113, the driving assist sensor 114 and the CAN 115 (a step S11). For example, the information receiving unit 121 receives the biological information that is one specific example of the occupant information from the detect apparatus 111. For example, the information receiving unit 121 receives the occupant information that is unique to the navigation operation from the navigation apparatus 112. For example, the information receiving unit 121 receives the personal information that is one specific example of the occupant information from the personal information DB 113. For example, the information receiving unit 121 receives the information relating to the condition of the vehicle 1 that is one specific example of the occupant information from each of the driving assist sensor 114 and the CAN 115.

Then, the toilet desire estimating unit 122 estimates at least one of the desire of the occupant to urinate and the desire of the occupant to defecate (namely, the toilet desire of the occupant) on the basis of the occupant information received by the information receiving unit 121 at the step S11 (a step S12). As described above, the occupant information received by the information receiving unit 121 at the step S11 is the information that has some relation with at least one of the desire of the occupant to urinate and the desire of the occupant to defecate. Thus, the toilet desire estimating unit 122 is capable of estimating at least one of the desire of the occupant to urinate and the desire of the occupant to defecate on the basis of the occupant information.

The operation of estimating at least one of the desire to urinate and the desire to defecate may include an operation of estimating at least one of the current desire of the occupant to urinate and the current desire of the occupant to defecate. In this case, the toilet desire estimating unit 122 may estimate whether or not the occupant feels at least one of the desire to urinate and the desire to defecate now. Note that "at least one of the current desire to urinate and the current desire to defecate" in the present embodiment may mean at least one of the desire to urinate and the desire to defecate at a timing when the information receiving unit 121 receives the occupant information.

The operation of estimating at least one of the desire to urinate and the desire to defecate may include an operation of estimating an intensity (in other words, a strength) of at least one of the desire to urinate and the desire to defecate which the occupant feels now. For example, the toilet desire estimating unit 122 may estimate an intensity score (in other words, a strength score) that represents the intensity of at least one of the desire to urinate and the desire to defecate which the occupant feels now. For example, the toilet desire estimating unit 122 may estimate which of a plurality of intensity levels the intensity of at least one of the desire to urinate and the desire to defecate which the occupant feels now belongs to.

The operation of estimating at least one of the desire to urinate and the desire to defecate may include an operation of estimating at least one of the future desire of the occupant to urinate and the future desire of the occupant to defecate, in addition to or instead of the operation of estimating at least one of the current desire of the occupant to urinate and the current desire of the occupant to defecate. For example, the toilet desire estimating unit 122 may estimate when the occupant feels at least one of the desire to urinate and the desire to defecate under the situation where the occupant does not yet feel at least one of the desire to urinate and the desire to defecate now. For example, the toilet desire estimating unit 122 may estimate whether or not the occupant feels at least one of the desire to urinate and the desire to defecate in the near future under the situation where the occupant does not yet feel at least one of the desire to urinate and the desire to defecate now. Note that "at least one of the future desire to urinate and the future desire to defecate" in the present embodiment may mean at least one of the desire to urinate and the desire to defecate in the future than the timing when the information receiving unit 121 receives the occupant information.

The operation of estimating at least one of the desire to urinate and the desire to defecate may include an operation of estimating the intensity of at least one of the desire to urinate and the desire to defecate that is estimated to be felt by the occupant in the future. Note that the operation of estimating the intensity of at least one of the desire to urinate and the desire to defecate may include an operation of estimating the intensity score that represents the intensity of at least one of the desire to urinate and the desire to defecate and may include an operation of estimating which of the plurality of intensity levels the intensity of at least one of the desire to urinate and the desire to defecate belongs to, as described above. For example, the toilet desire estimating unit 122 may estimate the intensity of at least one of the desire to urinate and the desire to defecate at a desired timing in the future that is estimated to be felt by the occupant in the future under the situation where the occupant does not yet feel at least one of the desire to urinate and the desire to defecate now. For example, the toilet desire estimating unit 122 may estimate how the intensity of at least one of the desire to urinate and the desire to defecate that is estimated to be felt by the occupant in the future varies as time elapses under the situation where the occupant does not yet feel at least one of the desire to urinate and the desire to defecate now. For example, the toilet desire estimating unit 122 may estimate how much the intensity of at least one of the desire to urinate and the desire to defecate is at a desired timing in the future under the situation where the occupant already feels at least one of the desire to urinate and the desire to defecate now. For example, the toilet desire estimating unit 122 may estimate how the intensity of at least one of the desire to urinate and the desire to defecate varies in the future (typically, how the intensity of at least one of the desire to urinate and the desire to defecate increases in the future) under the situation where the occupant already feels at least one of the desire to urinate and the desire to defecate now.

Note that the operation of estimating the future desire of the occupant to urinate under the situation where the occupant does not yet feel the desire to urinate corresponds to an operation of estimating the future desire of the occupant to urinate before the occupant feels (namely, is conscious of or is aware of) the desire to urinate. Similarly, the operation of estimating the future desire of the occupant to defecate under the situation where the occupant does not yet feel the desire to defecate corresponds to an operation of estimating the future desire of the occupant to defecate before the occupant feels (namely, is conscious of or is aware of) the desire to defecate.

The operation of estimating at least one of the desire to urinate and the desire to defecate may include an operation of estimating a time period from now during which the occupant can withstand at least one of the desire to urinate and the desire to defecate (namely, withstands at least one of an urge to urinate and an urge to defecate) that is already felt by the occupant now. The operation of estimating at least one of the desire to urinate and the desire to defecate may include an operation of estimating a time period from now or from a desired timing in the future during which the occupant can withstand at least one of the desire to urinate and the desire to defecate that is estimated to be felt by the occupant in the future. Note that there is a high possibility that the time period during which the occupant can withstand at least one of the desire to urinate and the desire to defecate becomes shorter as the intensity of at least one of the desire of the occupant to urinate and the desire of the occupant to defecate becomes stronger. Thus, it can be said that the operation of estimating the time period during which the occupant can withstand at least one of the desire to urinate and the desire to defecate corresponds to an operation of estimating the intensity of at least one of the desire of the occupant to urinate and the desire of the occupant to defecate in terms of a time. In this case, the toilet desire estimating unit 122 may estimate the intensity of at least one of the desire of the occupant to urinate and the desire of the occupant to defecate on the basis of the occupant information and estimate the time period during which the occupant can withstand at least one of the desire to urinate and the desire to defecate on the basis of the estimated intensity. Alternatively, the toilet desire estimating unit 122 may directly estimate the time period during which the occupant can withstand at least one of the desire to urinate and the desire to defecate on the basis of the occupant information.

The toilet desire estimating unit 122 may estimate at least one of the desire of the occupant to urinate and the desire of the occupant to defecate by using a calculation model (for example, a calculation model using a neural network) to which the occupant information is inputted as an input information and from which the result of estimating at least one of the desire of the occupant to urinate and the desire of the occupant to defecate is outputted as an output information. This calculation model may be generated or learned on the basis of the occupant information that is received from a certain test subject person (alternatively, the actual occupant). This calculation model may be generated or learned on the basis of an information relating to at least one of the desire to urinate and the desire to defecate that is actually felt by the test subject person during the occupant information being received. Alternatively, for example, the toilet desire estimating unit 122 may estimate at least one of the desire of the occupant to urinate and the desire of the occupant to defecate by using a correlation information (for example, a table information and the like) that represents a correlation between the occupant information and at least one of the desire of the occupant to urinate and the desire of the occupant to defecate. This correlation information may be generated in advance on the basis of the occupant information that is received from a certain test subject person (alternatively, the actual occupant) and the information relating to at least one of the desire to urinate and the desire to defecate that is actually felt by the test subject person during the occupant information being received. The toilet desire estimating unit 122 may estimate at least one of the desire of the occupant to urinate and the desire of the occupant to defecate by using another estimating method, of course. Note that the estimating method used by the toilet desire estimating unit 122 (for example, each of the estimating method using the calculation model and the estimating method using the correlation information, as described above) may be improved by using the occupant information and the like an amount of which is massive to some extent (for example, a massive amount of the occupant information and the like that is equivalent to a big data), in order to improve an accuracy of estimating at least one of the desire of the occupant to urinate and the desire of the occupant to defecate on the basis of the occupant information.

Next, one specific example of the occupant information (namely, one specific example of each of the biological information, the occupant information that is unique to the navigation operation, the personal information and the information relating to the condition of the vehicle 1) and the reason why at least one of the desire to urinate and the desire to defecate is estimated on the basis of the occupant information will be described.

An information relating to a condition of an inside of a body of the occupant (for example, a condition of an organ that has a relation with at least one of an urination and a defecation) is one specific example of the biological information that has some relation with at least one of the desire of the occupant to urinate and the desire of the occupant to defecate. Specifically, a bladder is one specific example of the organ that has a relation with the urination. The bladder becomes larger (namely, enlarges or expands) as illustrated in FIG. 3A, when a urine is accumulated (in other words, collected) in the bladder. On the other hand, the bladder becomes smaller (namely, shrinks) as illustrated in FIG. 3B, when the urine is not accumulated (in other words, collected) in the bladder. Thus, there is a higher possibility that the occupant feels the desire to urinate when the bladder is relatively large, compared to the case where the bladder is relatively small. There is a high possibility that the occupant feels more intense (namely, stronger) desire to urinate as the bladder becomes larger. Moreover, it is possible to estimate, on the basis of the current size of the bladder and the like, how long the occupant starts to feel the desire to urinate even when the occupant does not yet feel the desire to urinate, because the bladder becomes larger as the amount of the urine accumulated in the bladder becomes larger. Moreover, it is possible to estimate, on the basis of the current size of the bladder and the like, how the intensity of the desire of the occupant to urinate varies as time elapses and the like, because the condition of the bladder varies from the current condition of the bladder. Thus, the information relating to the bladder (for example, the information relating to the size of the bladder (alternatively, a degree of an expansion of the bladder) is usable as the biological information used for estimating the desire of the occupant to urinate. Moreover, an information relating to a digestive organ (for example, at least one of a stomach, a small intestine and a large intestine) that is one specific example of the organ having a relation with at least one of the urination and the defecation is usable as the biological information used for estimating at least one of the desire of the occupant to urinate and the desire of the occupant to defecate, for the same reason. In this case, it is preferable that the detect apparatus 111 include a detect apparatus that is configured to detect the condition of the inside of the body of the occupant. At least one of an ultrasonic sensor (what we call an echo-graphic apparatus) and a millimeter-wave sensor is one specific example of the detect apparatus that is configured to detect the condition of the inside of the body of the occupant.

Figure 5:
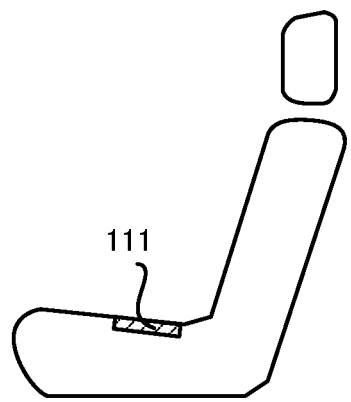
FIG. 5 is a cross-sectional view that illustrates a detect apparatus that is placed at a seating surface of a seat of a vehicle.

An information relating to a condition of a specific muscle of the occupant (for example, a condition of the muscle that has a relation with at least one of the urination and the defecation) is one specific example of the biological information that has some relation with at least one of the desire of the occupant to urinate and the desire of the occupant to defecate. Specifically, a urinary sphincter is one specific example of the muscle that has a relation with the urination. The urinary sphincter is tighten so as to close a urethra as illustrated in FIG. 4A, when the bladder is now accumulating the urine. On the other hand, the urinary sphincter is relaxed more as the amount of the urine accumulated in the bladder becomes larger. As a result, the urine is excreted from the bladder after the urinary sphincter is relaxed to some extent as illustrated in FIG. 4B. Thus, there is a higher possibility that the occupant feels the desire to urinate when the urinary sphincter is relaxed relatively, compared to the case where the urinary sphincter is tightened relatively. There is a high possibility that the occupant feels more intense (namely, stronger) desire to urinate as the urinary sphincter is relaxed larger. Moreover, it is possible to estimate, on the basis of a current relaxing degree (in other words, a current tightening degree) of the urinary sphincter and the like, how long the occupant starts to feel the desire to urinate and the like even when the occupant does not yet feel the desire to urinate, because the urine is excreted from the bladder after the urinary sphincter is relaxed to some extent. Moreover, it is possible to estimate, on the basis of the current relaxing degree (in other words, the current tightening degree) of the urinary sphincter and the like, how the intensity of the desire of the occupant to urinate varies as time elapses and the like, because the condition of the urinary sphincter varies from the current relaxing degree of the urinary sphincter. Thus, the information relating to the urinary sphincter (for example, the information relating to the relaxing degree of the urinary sphincter) is usable as the biological information used for estimating the desire of the occupant to urinate. Moreover, an information relating to an anal sphincter that is one specific example of the muscle having a relation with the defecation is usable as the biological information used for estimating the desire of the occupant to defecate, for the same reason. Moreover, it can be said that a muscle of a hip (namely, a gluteus, and at least one of a gluteus maximus, a gluteus medius and a gluteus minimus) is one specific example of the muscle that has a relation with the defecation, because there is a high possibility that the muscle of the hip moves when the anal sphincter moves. This is because there is a possibility that the gluteus moves to close an anus when the occupant withstands the defecation (namely, withstands the desire to defecate). Thus, an information relating to the gluteus is usable as the biological information used for estimating the desire of the occupant to defecate. In this case, it is preferable that the detect apparatus 111 include a detect apparatus that is configured to detect the condition of the specific muscle of the occupant. At least one of a pressure sensor that is configured to detect the condition of the muscle as an action of the muscle and a myoelectric sensor that is configured to detect the condition of the muscle as a myoelectric potential is one specific example of the detect apparatus that is configured to detect the condition of the specific muscle of the occupant. In this case, as illustrated in FIG. 5, the detect apparatus 111 may be placed at a seat surface of a seat of the vehicle 1 that is near at least one of the sphincter and the gluteus. Alternatively, the occupant may wear the detect apparatus 111.

An information relating to a fart of the occupant is one specific example of the biological information that has some relation with at least one of the desire of the occupant to urinate and the desire of the occupant to defecate. Specifically, there is a higher possibility that the occupant farts when the occupant feels the desire to defecate, compared to the case where the occupant does not feel the desire to defecate. Alternatively, there is a high possibility that the occupant feels the desire to defecate more as a food eaten by the occupant is digested more (especially, the food is digested more in a lower part of the small intestine and the large intestine), and there is a high possibility that the occupant farts in this condition. Therefore, there is a higher possibility that the occupant feels the desire to defecate when the occupant farts with a relatively high frequency, compared to the case where the occupant farts with a relatively low frequency or the occupant does not fart. There is a high possibility that the occupant feels more intense (namely, stronger) desire to defecate as the frequency with which the occupant farts becomes higher. Moreover, it is possible to estimate, on the basis of the current frequency with which the occupant farts and the like, how long the occupant starts to feel the desire to defecate and the like even when the occupant does not yet feel the desire to defecate, because there is a high possibility that the occupant farts when the occupant feels the desire to defecate. Moreover, it is possible to estimate, on the basis of the current frequency with which the occupant farts and the like, how the intensity of the desire of the occupant to defecate varies as time elapses under an assumption that the frequency with which the occupant farts and the like varies depending on the intensity of the desire to defecate. Moreover, it is possible to estimate, on the basis of a current characteristics of the fart (for example, a gas component in the fart, a concentration of the gas, a degree of an odor of the fart and a sound of the fart) of the occupant, the desire of the occupant to defecate under an assumption that the characteristics of the fart of the occupants varies depending on the desire to defecate. Thus, the information relating to the fart of the occupant is usable as the biological information used for estimating the desire of the occupant to defecate. In this case, it is preferable that the detect apparatus 111 include a detect apparatus that is configured to detect the fart of the occupant. A gas sensor that is configured to detect the fart excreted as the gas is one specific example of the detect apparatus that is configured to detect the fart of the occupant. In this case, as illustrated in FIG. 5, the detect apparatus 111 may be placed at the seat surface of the seat of the vehicle 1 that is near the anus of the occupant. Alternatively, the occupant may wear the detect apparatus 111.

An information relating to a condition of a brain of the occupant (for example, an information relating to an activity condition of the brain) is one specific example of the biological information that has some relation with at least one of the desire of the occupant to urinate and the desire of the occupant to defecate. Specifically, when the urine is accumulated in the bladder, a stretch stimulus of a bladder wall is transmitted to the brain through a spinal cord as the desire to urinate. Moreover, when a stool is accumulated in the large intestine, a stretch stimulus of a large intestine wall is transmitted to the brain through the spinal cord as the desire to defecate. Moreover, when these stimulus is transmitted to the brain, a urinary reflex and/or a defecation reflex occurs due to an order from the brain and the sphincter is relaxed to urinate and/or defecate. Therefore, it is possible to estimate, on the basis of the condition of the brain of the occupant, whether or not the occupant feels at least one of the desire to urinate and the desire to defecate. It is possible to estimate, on the basis of the condition of the brain of the occupant, the intensity of at least one of the desire to urinate and the desire to defecate that is felt by the occupant. Moreover, there is a possibility that some stimulus based on the current condition of the bladder and the like is transmitted to the brain, even when the occupant does not yet feel at least one of the desire to urinate and the desire to defecate now. Thus, it is possible to estimate, on the basis of the current condition of the brain of the occupant, how long the occupant starts to feel at least one of the desire to urinate and the desire to defecate and/or how the intensity of at least one of the desire to urinate and the desire to defecate varies as time elapses and the like, even when the occupant does not yet feel at least one of the desire to urinate and the desire to defecate now. Thus, the information relating to the condition of the brain of the occupant is usable as the biological information used for estimating at least one of the desire of the occupant to urinate and the desire of the occupant to defecate. In this case, it is preferable that the detect apparatus 111 include a detect apparatus that is configured to detect the condition of the brain of the occupant. At least one of a brain wave sensor that is configured to detect a brain wave, a blood flow sensor that is configured to detect a blood flow of the brain and an imaging apparatus that is configured to capture an image (for example, a cross-sectional image) of the brain is one specific example of the detect apparatus that is configured to detect the condition of the brain of the occupant. Also in this case, the detect apparatus 111 may be placed at the vehicle 1 and the occupant may wear the detect apparatus 111.

Figure 6:
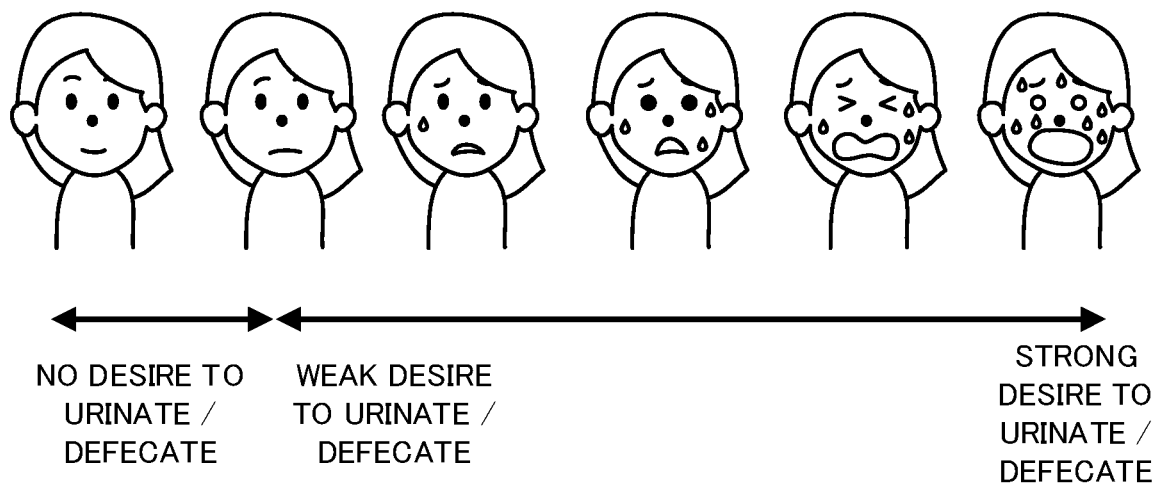
FIG. 6 is a diagram that illustrates a relationship between a facial expression of an occupant and at least one of a desire to urinate and a desire to defecate.

An information relating to a facial expression of the occupant is one specific example of the biological information that has some relation with at least one of the desire of the occupant to urinate and the desire of the occupant to defecate. Specifically, as illustrated in FIG. 6, there is a possibility that the facial expression of the occupant changes due to at least one of the desire to urinate and the desire to defecate when the occupant feels at least one of the desire to urinate and the desire to defecate. There is a possibility that the facial expression when at least one of the desire to urinate and the desire to defecate is relatively strong is different from the facial expression when at least one of the desire to urinate and the desire to defecate is relatively weak. Therefore, it is possible to estimate, on the basis of the facial expression of the occupant, whether or not the occupant feels at least one of the desire to urinate and the desire to defecate. It is possible to estimate, on the basis of the facial expression of the occupant, the intensity of at least one of the desire to urinate and the desire to defecate that is felt by the occupant. Moreover, there is a possibility that the facial expression of the occupant changes depending on an amount of the urine accumulated in the bladder and/or an amount of the stool accumulated in the large intestine, even when the occupant does not yet feel at least one of the desire to urinate and the desire to defecate now. Thus, it is possible to estimate, on the basis of the current facial expression of the occupant, how long the occupant starts to feel at least one of the desire to urinate and the desire to defecate and/or how the intensity of at least one of the desire of the occupant to urinate and the desire of the occupant to defecate varies as time elapses and the like, even when the occupant does not yet feel at least one of the desire to urinate and the desire to defecate now. Thus, the information relating to the facial expression of the occupant is usable as the biological information used for estimating at least one of the desire of the occupant to urinate and the desire of the occupant to defecate. In this case, it is preferable that the detect apparatus 111 include a detect apparatus that is configured to detect the facial expression of the occupant. A camera that is configured to image a face of the occupant is one specific example of the detect apparatus that is configured to detect the facial expression of the occupant.

An information relating to a voice of the occupant is one specific example of the biological information that has some relation with at least one of the desire of the occupant to urinate and the desire of the occupant to defecate. Specifically, there is a possibility that the occupant makes a voice such as "I want to go to a restroom", "Oh, I almost pee my pants" (namely, a voice that directly or indirectly indicates an intention to feel at least one of the desire to urinate and the desire to defecate) when the occupant feels at least one of the desire to urinate and the desire to defecate. Namely, there is a possibility that the occupant indicates, as a voice, the intention to feel at least one of the desire to urinate and the desire to defecate when the occupant feels at least one of the desire to urinate and the desire to defecate. Thus, the information relating to the voice of the occupant is usable as the biological information used for estimating at least one of the desire of the occupant to urinate and the desire of the occupant to defecate. In this case, it is preferable that the detect apparatus 111 include a detect apparatus that is configured to detect the voice of the occupant. A microphone is one specific example of the detect apparatus that is configured to detect the voice of the occupant.

Incidentally, it can be said that the toilet desire estimating unit 122 estimates at least one of the desire of the occupant to urinate and the desire of the occupant to defecate before the occupant indicates the intention to feel at least one of the desire to urinate and the desire to defecate when the information relating to the voice of the occupant is not used as the occupant information used for estimating at least one of the desire to urinate and the desire to defecate. Thus, the operation of estimating at least one of the desire of the occupant to urinate and the desire of the occupant to defecate may include an operation of estimating at least one of the desire of the occupant to urinate and the desire of the occupant to defecate before the occupant indicates the intention to feel at least one of the desire to urinate and the desire to defecate.

An information relating to a motion of the body (in other words, a behavior or a motion) of the occupant is one specific example of the biological information that has some relation with at least one of the desire of the occupant to urinate and the desire of the occupant to defecate. Specifically, there is a possibility that the occupant makes a unique motion such as a motion of a squirm when the occupant feels at least one of the desire to urinate and the desire to defecate. Moreover, there is a possibility that the motion of the body of the occupant changes depending on the amount of the urine accumulated in the bladder and/or the amount of the stool accumulated in the large intestine, even when the occupant does not yet feel at least one of the desire to urinate and the desire to defecate now. Thus, the information relating to the motion of the body of the occupant is usable as the biological information used for estimating at least one of the desire of the occupant to urinate and the desire of the occupant to defecate. In this case, it is preferable that the detect apparatus 111 include a detect apparatus that is configured to detect the motion of the body of the occupant. At least one of a camera that is configured to image the body of the occupant, an electromagnetic wave sensor that is configured to detect the motion of the body of the occupant by an electromagnetic wave (for example, the millimeter wave), an optical sensor that is configured to detect the motion of the body of the occupant by a light and a myoelectric sensor that is configured to detect the motion of the body of the occupant as the myoelectric potential is one specific example of the detect apparatus that is configured to detect the motion of the body of the occupant.

An information relating to a history of the traveling of the vehicle 1 (namely, a history of the movement of the occupant) is one specific example of the occupant information that has some relation with at least one of the desire of the occupant to urinate and the desire of the occupant to defecate and that is unique to the navigation operation. This is because there is a high possibility that the vehicle 1 is parked at a place having a restroom in order to allow the occupant to take a restroom brake when the occupant feels at least one of the desire to urinate and the desire to defecate. In this case, the toilet desire estimating unit 122 is capable of estimating, on the basis of the history of the traveling of the vehicle 1, a cycle with which the occupant takes the restroom break (namely, a cycle with which the occupant feels at least one of the desire to urinate and the desire to defecate). As a result, the toilet desire estimating unit 122 is capable of estimating at least one of the desire of the occupant to urinate and the desire of the occupant to defecate on the basis of the estimated cycle and a time at which the occupant takes the last restroom brake. For example, the toilet desire estimating unit 122 is capable of estimating at least one of the current desire of the occupant to urinate and the current desire of the occupant to defecate by determining which timing in the cycle that starts from the time at which the occupant takes the last restroom brake corresponds to the current timing. For example, the toilet desire estimating unit 122 is capable of estimating at least one of the future desire of the occupant to urinate and the future desire of the occupant to defecate by determining which timing in the cycle that starts from the time at which the occupant takes the last restroom brake corresponds to a certain timing in the future.

An action information relating to an action of the occupant is one specific example of the personal information that has some relation with at least one of the desire of the occupant to urinate and the desire of the occupant to defecate. This is because there is a high possibility that the occupant takes an action for reducing at least one of the desire to urinate and the desire to defecate when the occupant feels at least one of the desire to urinate and the desire to defecate and/or there is a high possibility that the occupant feels at least one of the desire to urinate and the desire to defecate due to an action of some kind of the occupant. In this case, the toilet desire estimating unit 122 is capable of estimating at least one of the desire of the occupant to urinate and the desire of the occupant to defecate on the basis of the action information.

An action history information relating to a history of the action of the occupant is one specific example of the action information. A sleeping history information relating to a history of a sleeping of the occupant is one specific example of the action history information. This is because there is a high possibility that a human feels at least one of the desire to urinate and the desire to defecate when the human wakes up or goes to bed, generally. In this case, the toilet desire estimating unit 122 is capable of estimating, on the basis of the sleeping history information, a time at which the occupant is likely to feel at least one of the desire to urinate and the desire to defecate. As a result, the toilet desire estimating unit 122 is capable of estimating at least one of the desire of the occupant to urinate and the desire of the occupant to defecate under an assumption that a lifestyle of the occupant does not change (for example, the occupant wakes up and goes to bet at the same time every day). A diet history information relating to a history of a diet (in other words, a food or a meal) eaten by the occupant is one specific example of the action history information. This is because there is a high possibility that the occupant feels at least one of the desire to urinate and the desire to defecate after a predetermined time elapses from a timing at which the occupant eats the diet. In this case, the toilet desire estimating unit 122 is capable of estimating, on the basis of the diet history information, the time at which the occupant is likely to feel at least one of the desire to urinate and the desire to defecate. As a result, the toilet desire estimating unit 122 is capable of estimating at least one of the desire of the occupant to urinate and the desire of the occupant to defecate under an assumption that the lifestyle of the occupant does not change (for example, the occupant always eats the diet at the same time). An excretion history information relating to a history of an excretion (in other words, the urination and/or the defecation) of the occupant is one specific example of the action history information. This is because there is a high possibility that the occupant excretes the urine and/or the stool (namely, the occupant feels at least one of the desire to urinate and the desire to defecate) at a same period of time if the lifestyle does not change. In this case, the toilet desire estimating unit 122 is capable of estimating, on the basis of the excretion history information, the time at which the occupant is likely to feel at least one of the desire to urinate and the desire to defecate. As a result, the toilet desire estimating unit 122 is capable of estimating at least one of the desire of the occupant to urinate and the desire of the occupant to defecate under an assumption that the lifestyle of the occupant does not change (for example, the occupant always excretes the urine and/or the stool at the same time).

A schedule information relating to a schedule of the occupant is another one specific example of the action information. This is because there is a high possibility that the occupant (for example, as driver of a truck and the like) makes the schedule that schedules in advance the place at which the occupant takes the restroom break, when the occupant makes the schedule. In this case, the toilet desire estimating unit 122 is capable of estimating, on the basis of the schedule information, a time at which the occupant takes the restroom break (namely, the occupant goes to the restroom). There is a high possibility that the time at which the occupant takes the restroom break corresponds to a time at which it is expected that the occupant feels at least one of the desire to urinate and the desire to defecate. As a result, the toilet desire estimating unit 122 is capable of estimating at least one of the desire of the occupant to urinate and the desire of the occupant to defecate under an assumption that the occupant keeps on the schedule.

An information relating to a break frequency, an acceleration rate of the vehicle 1 and an inter-vehicular distance is one specific example of the occupant information that has some relation with at least one of the desire of the occupant to urinate and the desire of the occupant to defecate and that is relating to the condition of the vehicle 1. This is because there is a high possibility that the occupant drives the vehicle 1 in a relatively aggressive driving style, a relatively hurried driving style or a relatively rushed driving style when the occupant feels at least one of the desire to urinate and the desire to defecate. In this case, the toilet desire estimating unit 122 is capable of determining the driving style of the occupant on the basis of the condition of the vehicle 1 and estimating at least one of the desire of the occupant to urinate and the desire of the occupant to defecate by determining whether or not the determined driving style is the relatively aggressive driving style, the relatively hurried driving style or the relatively rushed driving style that is not usually observed (namely, the driving style that is observed when the occupant feels at least one of the desire to urinate and the desire to defecate).

The toilet desire estimating unit 122 may estimate at least one of the desire of the occupant to urinate and the desire of the occupant to defecate on the basis of one type of the occupant information. Alternatively, the toilet desire estimating unit 122 may estimate at least one of the desire of the occupant to urinate and the desire of the occupant to defecate on the basis of a plurality of types of the occupant information. For example, the toilet desire estimating unit 122 may estimate at least one of the desire of the occupant to urinate and the desire of the occupant to defecate by using the calculation model to which the plurality of types of the occupant information are inputted as the input information and from which the result of estimating at least one of the desire of the occupant to urinate and the desire of the occupant to defecate is outputted as the output information. For example, the toilet desire estimating unit 122 may estimate at least one of the desire of the occupant to urinate and the desire of the occupant to defecate by using the correlation information that represents a correlation between the plurality of types of the occupant information and at least one of the desire of the occupant to urinate and the desire of the occupant to defecate. For example, the toilet desire estimating unit 122 may estimate at least one of the desire of the occupant to urinate and the desire of the occupant to defecate by executing a predetermined data processing (for example, an averaging processing, a weighted-averaging processing and the like) on the plurality of output information outputted from a plurality of calculation models to which the plurality of types of the occupant information are inputted, respectively (namely, a plurality of estimated results based on the plurality of types of the occupant information). For example, the toilet desire estimating unit 122 may obtain the plurality of estimated results by using a plurality of table information that correspond to the plurality of types of the occupant information, respectively, and estimate at least one of the desire of the occupant to urinate and the desire of the occupant to defecate by executing a predetermined data processing (for example, an averaging processing, a weighted-averaging processing and the like) on the plurality of estimated results.

Again in FIG. 2, then, the assist executing unit 123 determines, on the basis of the estimated result of the toilet desire estimating unit 122 (namely, a result of estimating at least one of the desire of the occupant to urinate and the desire of the occupant to defecate) at the step S12, the content of the occupant assist that is to be executed (a step S13). Then, the assist executing unit 123 executes the occupant assist having the content determined at the step S13 (a step S14). However, when it is determined at the step S13 that the occupant assist may not be executed necessarily, the assist executing unit 123 may not execute the occupant assist necessarily at the step S14.

A break assist for proposing the occupant (alternatively, a driver when the occupant is not the driver) to take the restroom break by using the display 131 (alternatively, any HMI (Human Machine Interface) other than the display 131) is one specific example of the occupant assist. In this case, the occupant has an advantage of taking the restroom break easily. For example, when it is estimated that the occupant feels at least one of the desire to urinate and the desire to defecate now, the assist executing unit 123 may execute the break assist for proposing the occupant to take the restroom break quickly (alternatively, as soon as possible). For example, when it is estimated that the occupant feels at least one of the desire to urinate and the desire to defecate at a certain timing in the future, the assist executing unit 123 may execute the break assist for proposing the occupant now to take the restroom break in the certain timing in the future or may execute the break assist for proposing the occupant at the certain timing in the future (alternatively, before the certain timing in the future) to take the restroom break in the certain timing in the future. In this case, the assist executing unit 123 may change the content of the break assist on the basis of the intensity of at least one of the desire of the occupant to urinate and the desire of the occupant to defecate. For example, the assist executing unit 123 may execute the break assist for proposing the occupant to take the restroom break sooner as at least one of the desire of the occupant to urinate and the desire of the occupant to defecate is stronger. For example, the assist executing unit 123 may execute the break assist for proposing the occupant to take the restroom break before the time period during which the occupant can withstand at least one of the desire to urinate and the desire to defecate elapses. On the other hand, the assist executing unit 123 may not execute the break assist when it is estimated that the occupant does not yet feel at least one of the desire to urinate and the desire to defecate.

The break assist may include an assist for presenting an information relating to the restroom that is proposed by the break assist. The information relating to the restroom may include an information relating to a location of the restroom and an information relating to a name of the restroom. In this case, the occupant has an advantage of reaching the restroom without getting lost on the way. The break assist may include an assist for presenting an information relating to a time needed for the occupant to reach the restroom that is proposed by the break assist. In this case, the occupant has an advantage of relieving a concern that the occupant does not know when the occupant reaches the restroom. The break assist may include an assist for presenting an information relating to a congestion degree (for example, a current congestion degree, a future congestion degree and/or a congestion degree at a time at which it is expected that the occupant reaches the restroom) of the restroom that is proposed by the break assist. In this case, the occupant has an advantage of relieving a concern that the occupant does not know whether the restroom which the occupant intends to use is really available to the occupant.

When the restroom that is proposed by the break assist is a restroom allowed to be reserved (for example, a restroom using a system that allows a reservation online), the break assist may include an assist for automatically reserving the restroom that is proposed by the break assist. For example, the break assist may include an assist for automatically reserving the restroom so that the restroom is available at a time when it is expected that the occupant reaches the restroom. In this case, the occupant has an advantage of more likely to use the restroom surely when the occupant reaches the restroom. Moreover, when the restroom that is proposed by the break assist is a restroom allowed to be reserved, the break assist may include an assist for presenting an information relating to another person who reserves the restroom that is proposed by the break assist. The information relating to another person may include an information relating to the intensity of at least one of the desire of another person to urinate and the desire of another person to defecate (namely, an information that indicating whether or not another person feels the urgent desire to urinate and/or defecate). In this case, the occupant has an advantage of easily yielding to and/or being yielded by another person.

A break route propose assist for proposing, to the occupant (alternatively, the driver when the occupant is not the driver or the vehicle 1 when the vehicle 1 is an autonomous vehicle), a recommended route that allows the occupant to take the restroom break more easily than another driving route (for example, a driving route that is scheduled now) as a driving route along which the vehicle 1 is to travel by using the display 131 or any HMI is another one specific example of the occupant assist. A driving route that allows the vehicle 1 to pass through a place having the restroom (alternatively, a place near the restroom, same applies to the following description) is one specific example of the recommended route that allows the occupant to take the restroom break more easily. This is because the occupant is allowed to take the restroom break more easily when the vehicle 1 passes through the place having the restroom, compared to the case where the vehicle 1 passes through the place not having the restroom. In this case, the occupant has an advantage of taking the restroom break easily. For example, when it is estimated that the occupant feels at least one of the desire to urinate and the desire to defecate now, the assist executing unit 123 may execute the break route propose assist for proposing the recommended route that allows the occupant to take the restroom break quickly (alternatively, as soon as possible). For example, when it is estimated that the occupant feels at least one of the desire to urinate and the desire to defecate at a certain timing in the future, the assist executing unit 123 may execute the break route propose assist for proposing the recommended route that allows the occupant to take the restroom break in the certain timing in the future (alternatively, before the certain timing in the future). In this case, the assist executing unit 123 may change the content of the break route propose assist on the basis of the intensity of at least one of the desire of the occupant to urinate and the desire of the occupant to defecate. For example, the assist executing unit 123 may execute the break route propose assist for proposing the recommended route that allows the occupant to take the restroom break sooner as at least one of the desire of the occupant to urinate and the desire of the occupant to defecate is stronger. For example, the assist executing unit 123 may execute the break route propose assist for proposing the recommended route that allows the occupant to take the restroom break before the time period during which the occupant can withstand at least one of the desire to urinate and the desire to defecate elapses. On the other hand, the assist executing unit 123 may not execute the break route propose assist when it is estimated that the occupant does not yet feel at least one of the desire to urinate and the desire to defecate.

The break route propose assist may include an assist for presenting an information relating to the restroom that is expected to be used by the occupant in the break route propose assist, as with the break assist. The break route propose assist may include an assist for presenting an information relating to the time needed for the occupant to reach the restroom that is expected to be used by the occupant in the break route propose assist, as with the break assist. The break route propose assist may include an assist for presenting an information relating to the congestion degree of the restroom that is expected to be used by the occupant in the break route propose assist, as with the break assist. The break route propose assist may include an assist for automatically reserving the restroom that is expected to be used by the occupant in the break route propose assist, as with the break assist. The break route propose assist may include an assist for presenting an information relating to another person who reserves the restroom that is expected to be used by the occupant in the break route propose assist, as with the break assist.

A stable route propose assist for proposing, to the occupant, the driver or the vehicle 1, a recommended route that allows a vibration of the vehicle 1 to be smaller than the vibration of the vehicle 1 traveling along another driving route (for example, the driving route that is scheduled now) (namely, that allows the vehicle 1 to be more stable than the vehicle 1 traveling along another driving route) as a driving route along which the vehicle 1 is to travel by using the display 131 or any HMI is another one specific example of the occupant assist. A driving route that allows at least one of a longitudinal acceleration (in other words, an acceleration in front to rear direction), a vertical acceleration (in other words, an acceleration in up to low direction) and a lateral acceleration (in other words, an acceleration in side to side direction) of the vehicle 1 to be smaller is one specific example of the recommended route that allows the vibration of the vehicle 1 to be smaller. A driving route in which an inclination of a road is relatively small and/or a curvature of the road is relatively small is one specific example of the recommended route that allows the vibration of the vehicle 1 to be smaller. There is a possibility that a stimulation that increases at least one of the desire of the occupant to urinate and the desire of the occupant to defecate (for example, at least one of the stretch stimulus that caused by the urine accumulated in the bladder hitting the bladder wall, the stretch stimulus that caused by the stool accumulated in the large intestine hitting the large intestine wall and a stimulus that is caused by an acceleration applied to the occupant so that the sphincter is relaxed). Therefore, there is a high possibility that the vehicle 1 travels so that at least one of the desire of the occupant to urinate and the desire of the occupant to defecate does not increase more and/or at least one of the desire of the occupant to urinate and the desire of the occupant to defecate is eased, which is an advantage. For example, when it is estimated that the occupant feels at least one of the desire to urinate and the desire to defecate now, the assist executing unit 123 may execute the stable route propose assist for proposing the recommended route that allows the vehicle 1 to travel so that the vibration of the vehicle 1 is smaller for a while from now (for example, until the vehicle 1 reaches the place having the restroom, same applies to the following description). For example, when it is estimated that the occupant feels at least one of the desire to urinate and the desire to defecate at a certain timing in the future, the assist executing unit 123 may execute the stable route propose assist for proposing the recommended route that allows the vehicle 1 to travel so that the vibration of the vehicle 1 is smaller for a while from the certain timing in the future (alternatively, from a timing before the certain timing in the future by a predetermined time). In this case, the assist executing unit 123 may change the content of the stable route propose assist on the basis of the intensity of at least one of the desire of the occupant to urinate and the desire of the occupant to defecate. For example, the assist executing unit 123 may execute the stable route propose assist for proposing the recommended route that allows the vehicle 1 to start traveling along the driving route by which the vibration of the vehicle 1 is smaller sooner as at least one of the desire of the occupant to urinate and the desire of the occupant to defecate is stronger. For example, the assist executing unit 123 may execute the stable route propose assist for proposing the recommended route that allows the vehicle 1 to start traveling along the driving route by which the vibration of the vehicle 1 is smaller sooner as the time period during which the occupant can withstand at least one of the desire to urinate and the desire to defecate is shorter. On the other hand, the assist executing unit 123 may not execute the stable route propose assist when it is estimated that the occupant does not yet feel at least one of the desire to urinate and the desire to defecate.

Note that at least one of the break route propose assist and the stable route propose assist may include an assist for allowing the vehicle 1 to automatically travel along the recommended route by controlling the driving unit 132 (for example, the power source, the brake apparatus and the steering apparatus), in addition to or instead of the assist for proposing the recommended route by using the display 131.

A behavior assist for controlling the driving unit 132 to control a behavior of the vehicle 1 so that the vibration of the vehicle 1 when the driving unit 132 is controlled is smaller than the vibration of the vehicle 1 when the driving unit 132 is not controlled (namely, the behavior of the vehicle 1 when the driving unit 132 is controlled is more stable than the behavior of the vehicle 1 when the driving unit 132 is not controlled) is another one specific example of the occupant assist. A behavior in which at least one of the longitudinal acceleration, the vertical acceleration and the lateral acceleration of the vehicle 1 is smaller is one specific example of the behavior in which the vibration of the vehicle 1 is smaller. For example, there is a possibility that at least one of the longitudinal acceleration, the vertical acceleration and the lateral acceleration of the vehicle 1 becomes smaller when the behavior of the vehicle 1 is controlled so that the vehicle 1 is not accelerated, braked and/or turned suddenly. In this case, there is a high possibility that the vehicle 1 travels so that at least one of the desire of the occupant to urinate and the desire of the occupant to defecate does not increase more and/or at least one of the desire of the occupant to urinate and the desire of the occupant to defecate is eased, which is an advantage, as with the above described stable route propose assist. For example, when it is estimated that the occupant feels at least one of the desire to urinate and the desire to defecate now, the assist executing unit 123 may execute the behavior assist for controlling the behavior of the vehicle 1 so that the vibration of the vehicle 1 is smaller for a while from now. For example, when it is estimated that the occupant feels at least one of the desire to urinate and the desire to defecate at a certain timing in the future, the assist executing unit 123 may execute the behavior assist for controlling the behavior of the vehicle 1 so that the vibration of the vehicle 1 is smaller for a while from the certain timing in the future (alternatively, from a timing before the certain timing in the future by a certain time). In this case, the assist executing unit 123 may change the content of the behavior assist on the basis of the intensity of at least one of the desire of the occupant to urinate and the desire of the occupant to defecate. For example, the assist executing unit 123 may start to execute the behavior assist sooner as at least one of the desire of the occupant to urinate and the desire of the occupant to defecate is stronger. For example, the assist executing unit 123 may start to execute the behavior assist sooner as the time period during which the occupant can withstand at least one of the desire to urinate and the desire to defecate is shorter. On the other hand, the assist executing unit 123 may not execute the behavior assist when it is estimated that the occupant does not yet feel at least one of the desire to urinate and the desire to defecate.

An air conditioning assist for controlling the air conditioning apparatus 133 to control the temperature in the vehicle cabin of the vehicle 1 so that at least one of the desire of the occupant to urinate and the desire of the occupant to defecate does not increase more and/or at least one of the desire of the occupant to urinate and the desire of the occupant to defecate is eased is another one specific example of the occupant assist. Specifically, there is a possibility that the occupant is likely to feel the desire to urinate (moreover, the desire to defecate in some cases) and/or the desire of the occupant to urinate (moreover, the desire of the occupant to defecate) is likely to increase when the temperature in the vehicle cabin is too low. When the temperature in the vehicle cabin increases due to the air conditioning assist in this situation, there is a possibility that at least one of the desire of the occupant to urinate and the desire of the occupant to defecate does not increase easily and/or at least one of the desire of the occupant to urinate and the desire of the occupant to defecate is likely to be eased. Thus, the air conditioning assist allows at least one of the desire of the occupant to urinate and the desire of the occupant to defecate not to increase easily and/or at least one of the desire of the occupant to urinate and the desire of the occupant to defecate to be is eased easily, which is an advantage. For example, when it is estimated that the occupant feels at least one of the desire to urinate and the desire to defecate now, the assist executing unit 123 may start to execute the air conditioning assist quickly. For example, when it is estimated that the occupant feels at least one of the desire to urinate and the desire to defecate at a certain timing in the future, the assist executing unit 123 may start to execute the air conditioning assist from the certain timing in the future (alternatively, from a timing before the certain timing in the future by a predetermined time). In this case, the assist executing unit 123 may change the content of the air conditioning assist on the basis of the intensity of at least one of the desire of the occupant to urinate and the desire of the occupant to defecate. For example, the assist executing unit 123 may start to execute the air conditioning assist sooner as at least one of the desire of the occupant to urinate and the desire of the occupant to defecate is stronger. For example, the assist executing unit 123 may start to execute the air conditioning assist sooner as the time period during which the occupant can withstand at least one of the desire to urinate and the desire to defecate is shorter. On the other hand, the assist executing unit 123 may not execute the air conditioning assist when it is estimated that the occupant does not yet feel at least one of the desire to urinate and the desire to defecate.

A massage assist for controlling the massage apparatus 134 to massage the occupant so that at least one of the desire of the occupant to urinate and the desire of the occupant to defecate does not increase more and/or at least one of the desire of the occupant to urinate and the desire of the occupant to defecate is eased is another one specific example of the occupant assist. Specifically, it is known that there is an acupuncture point having a possibility that allows at least one of the desire of the occupant to urinate and the desire of the occupant to defecate not to increase more and/or at least one of the desire of the occupant to urinate and the desire of the occupant to defecate to be eased. At least one of a SP6 (Spleen Meridian of Foot Taiyin, San-In-Ko, SanYinJiao), an enuresis point, a diarrhea point and a LI4 (Large Intestine Meridian of Hand Yangming 4, Go-Koku) is one specific example of the acupuncture point. When the acupuncture point is massaged by the massage apparatus 134, there is a possibility that at least one of the desire of the occupant to urinate and the desire of the occupant to defecate does not increase easily and/or at least one of the desire of the occupant to urinate and the desire of the occupant to defecate is likely to be eased. Thus, the massage assist allows at least one of the desire of the occupant to urinate and the desire of the occupant to defecate not to increase easily and/or at least one of the desire of the occupant to urinate and the desire of the occupant to defecate to be eased easily, which is an advantage. For example, when it is estimated that the occupant feels at least one of the desire to urinate and the desire to defecate now, the assist executing unit 123 may start to execute the massage assist quickly. For example, when it is estimated that the occupant feels at least one of the desire to urinate and the desire to defecate at a certain timing in the future, the assist executing unit 123 may start to execute the massage assist from the certain timing in the future (alternatively, from a timing before the certain timing in the future by a predetermined time). In this case, the assist executing unit 123 may change the content of the massage assist on the basis of the intensity of at least one of the desire of the occupant to urinate and the desire of the occupant to defecate. For example, the assist executing unit 123 may start to execute the massage assist sooner as at least one of the desire of the occupant to urinate and the desire of the occupant to defecate is stronger. For example, the assist executing unit 123 may execute the massage assist so that the occupant is massaged by a stronger force as at least one of the desire of the occupant to urinate and the desire of the occupant to defecate is stronger. For example, the assist executing unit 123 may start to execute the massage sooner as the time period during which the occupant can withstand at least one of the desire to urinate and the desire to defecate is shorter. For example, the assist executing unit 123 may execute the massage assist so that the occupant is massaged by a stronger force as the time period during which the occupant can withstand at least one of the desire to urinate and the desire to defecate is shorter. On the other hand, the assist executing unit 123 may not execute the massage assist when it is estimated that the occupant does not yet feel at least one of the desire to urinate and the desire to defecate.

(3) Technical Effect

As described above, the toilet desire estimating unit 122 is capable of estimating at least one of the desire of the occupant to urinate and the desire of the occupant to defecate on the basis of the occupant information. Moreover, the assist executing unit 123 is capable of executing the appropriate occupant assist on the basis of the estimated result of the toilet desire estimating unit 122.

Especially in the present embodiment, the toilet desire estimating unit 122 is capable of estimating at least one of the future desire of the occupant to urinate and the future desire of the occupant to defecate. Therefore, the assist executing unit 123 is capable of executing the appropriate occupant assist based on the result of estimating at least one of the desire of the occupant to urinate and the desire of the occupant to defecate in the future than now. For example, the assist executing unit 123 is capable of executing the appropriate occupant assist now or at a certain timing in the future (alternatively, before a certain timing in the future), wherein the occupant assist is based on at least one of the desire of the occupant to urinate and the desire of the occupant to defecate at a certain timing in the future. Therefore, the assist executing unit 123 is capable of executing the more appropriate occupant assist based on at least one of the desire of the occupant to urinate and the desire of the occupant to defecate at a certain timing in the future, compared to an assist executing unit in a comparison example that is configured to start the occupant assist on a condition that the occupant feels (especially, is conscious of) at least one of the desire to urinate and the desire to defecate now.

Moreover, the toilet desire estimating unit 122 is capable of estimating at least one of the desire of the occupant to urinate and the desire of the occupant to defecate before the occupant is conscious of (namely, feels) at least one of the desire to urinate and the desire to defecate. For example, the toilet desire estimating unit 122 is capable of estimating when the occupant feels at least one of the desire to urinate and the desire to defecate and/or how strong the occupant feels at least one of the desire to urinate and the desire to defecate under the situation where the occupant is not yet conscious of at least one of the desire to urinate and the desire to defecate. Therefore, the assist executing unit 123 is capable of executing the more appropriate occupant assist based on the result of estimating at least one of the desire to urinate and the desire to defecate which the occupant is not yet conscious of. Namely, the assist executing unit 123 is capable of executing the more appropriate occupant assist based on at least one of the desire to urinate and the desire to defecate which the occupant is not yet conscious of, compared to the assist executing unit in the comparison example that is configured to start the occupant assist on a condition that the occupant feels (especially, is conscious of) at least one of the desire to urinate and the desire to defecate now.

Moreover, the toilet desire estimating unit 122 is capable of estimating at least one of the desire of the occupant to urinate and the desire of the occupant to defecate before the occupant indicates the intention (for example, indicates the intention by the voice) to feel at least one of the desire to urinate and the desire to defecate. Namely, the toilet desire estimating unit 122 is capable of estimating at least one of the actual desire to urinate and the actual desire to defecate of the occupant who does not indicate the intention to feel at least one of the desire to urinate and the desire to defecate. Note that at least one of the occupant who does not feel at least one of the desire to urinate and the desire to defecate, the occupant who does not conscious of at least one of the desire to urinate and the desire to defecate although the occupant really feels at least one of the desire to urinate and the desire to defecate, the occupant who pretends not to feel at least one of the desire to urinate and the desire to defecate and the occupant who cannot indicate the intention to feel at least one of the desire to urinate and the desire to defecate because of a sense of shame although the occupant really feels at least one of the desire to urinate and the desire to defecate is one specific example of the occupant who does not indicate the intention to feel at least one of the desire to urinate and the desire to defecate. Therefore, the assist executing unit 123 is capable of executing the appropriate occupant assist based on the result of estimating at least one of the actual desire to urinate and the actual desire to defecate of the occupant who does not indicate the intention to feel at least one of the desire to urinate and the desire to defecate. For example, the assist executing unit 123 may execute the occupant assist that proposes, the occupant who cannot indicate the intention to feel at least one of the desire to urinate and the desire to defecate because of a sense of shame although the occupant really feels at least one of the desire to urinate and the desire to defecate, taking the restroom brake behind the back of the surrounding person (for example, an assist for proposing the driver to reach the place having the restroom or an assist for allowing the vehicle 1 to automatically travel).

Moreover, the toilet desire estimating unit 122 is capable of estimating the intensity of at least one of the desire of the occupant to urinate and the desire of the occupant to defecate. Thus, the assist executing unit 123 is capable of executing the appropriate occupant assist based on the result of estimating the intensity of at least one of the desire to urinate and the desire to defecate.

(4) Modified Example

In the above described description, the information receiving unit 121 receives the occupant information from each of the detect apparatus 111, the navigation apparatus 112 and the personal information DB 113. However, the information receiving unit 121 does not necessarily receive the occupant information from at least one of the detect apparatus 111, the navigation apparatus 112 and the personal information DB 113. Namely, the information receiving unit 121 may not receive the occupant information from at least one of the detect apparatus 111, the navigation apparatus 112 and the personal information DB 113 and may receive the occupant information from at least another one of the detect apparatus 111, the navigation apparatus 112 and the personal information DB 113. In this case, the vehicle 1 does not necessarily have at least one the detect apparatus 111, the navigation apparatus 112 and the personal information DB 113.

In the above described description, the assist executing unit 123 execute at least one of the break assist, the break route propose assist and the stable route propose assist by using the display 131. However, the assist executing unit 123 does not necessarily execute the break assist, the break route propose assist and the stable route propose assist. In this case, the vehicle 1 does not necessarily have the display 131. In the above described description, the assist executing unit 123 execute the air conditioning assist by using the air conditioning apparatus 133. However, the assist executing unit 123 does not necessarily execute the air conditioning assist. In this case, the vehicle 1 does not necessarily have the air conditioning apparatus 133. In the above described description, the assist executing unit 123 execute the massage assist by using the massage apparatus 134. However, the assist executing unit 123 does not necessarily execute the massage assist. In this case, the vehicle 1 does not necessarily have the massage apparatus 134.

(5) Additional Statement

Relating to the above described embodiment, following additional statements will be disclosed.

(5-1) Additional Statement 1

An occupant assist apparatus according to the additional statement 1 is an occupant assist apparatus having: a receiving device that is configured to receive an occupant information relating to an occupant of a vehicle; an estimating device that is configured to estimate, on the basis of the occupant information, at least one of a desire of the occupant to urinate and a desire of the occupant to defecate in a future than a timing when the occupant information is received; and an executing device that is configured to execute an occupant assist on the basis of a result of an estimation by the estimating device.

Alternatively, an occupant assist apparatus according to the additional statement 1 may be an occupant assist apparatus having a controller, the controller is programmed to: receive an occupant information relating to an occupant of a vehicle; estimate, on the basis of the occupant information, at least one of a desire of the occupant to urinate and a desire of the occupant to defecate in a future than a timing when the occupant information is received; and execute an occupant assist on the basis of an estimated result.

The occupant assist apparatus according to the additional statement 1 is capable of estimating at least one of the desire of the occupant to urinate and the desire of the occupant to defecate in the future than now in advance. Thus, the occupant assist apparatus according to the additional statement 1 is capable of executing the appropriate occupant assist based on the result of estimating at least one of the desire of the occupant to urinate and the desire of the occupant to defecate in the future than now. Namely, the occupant assist apparatus according to the additional statement 1 is capable of estimating at least one of the desire of the occupant to urinate and the desire of the occupant to defecate and executing the occupant assist based on the estimated result more appropriately.

(5-2) Additional Statement 2

The occupant assist apparatus according to the additional statement 2 is the occupant assist apparatus according to the additional statement 1, wherein the estimating device is configured to (alternatively, the controller is programmed to) estimate, on the basis of the occupant information, at least one of the desire of the occupant to urinate and the desire of the occupant to defecate in the future than the timing when the occupant information is received before the occupant is conscious of at least one of the desire to urinate and the desire to defecate.

The occupant assist apparatus according to the additional statement 2 is capable of estimating at least one of the desire of the occupant to urinate and the desire of the occupant to defecate at a timing when the occupant is not yet conscious of (in other words, aware of) at least one of the desire to urinate and the desire to defecate. Namely, the occupant assist apparatus according to the additional statement 2 is capable of estimating at least one of the desire of the occupant to urinate and the desire of the occupant to defecate at a timing when the occupant does not yet feel at least one of the desire to urinate and the desire to defecate. Thus, the occupant assist apparatus according to the additional statement 2 is capable of executing the appropriate occupant assist based on the result of estimating at least one of the desire to urinate and the desire to defecate which the occupant is not yet conscious of.

(5-3) Additional Statement 3

The occupant assist apparatus according to the additional statement 3 is the occupant assist apparatus according to the additional statement 1 or 2, wherein the occupant information includes at least one of a biological information of the occupant and an action information relating to an action of the occupant.

The occupant assist apparatus according to the additional statement 3 is capable of appropriately estimating at least one of the desire of the occupant to urinate and the desire of the occupant to defecate on the basis of at least one of the biological information and the action information.

(5-4) Additional Statement 4

The occupant assist apparatus according to the additional statement 4 is the occupant assist apparatus according to the additional statement 3, wherein the action information includes at least one of a diet history information relating to a history of a diet eaten by the occupant and an excretion history information relating to a history of an excretion of the occupant.

The occupant assist apparatus according to the additional statement 4 is capable of appropriately estimating at least one of the desire of the occupant to urinate and the desire of the occupant to defecate on the basis of at least one of the diet history information and the excretion history information.

(5-5) Additional Statement 5

The occupant assist apparatus according to the additional statement 5 is the occupant assist apparatus according to any one of the additional statements 1 to 4, wherein the occupant assist includes at least one of (i) a break assist for proposing the occupant to take a restroom break, (ii) a route propose assist for proposing at least one of a first driving route that allows the vehicle to travel via a break spot at which the occupant is allowed to take a restroom break and a second driving route along that allows the vehicle to travel so as not to increase at least one of the desire of the occupant to urinate and the desire of the occupant to defecate than another driving route, (iii) a behavior assist for controlling a behavior of the vehicle so as not to increase at least one of the desire of the occupant to urinate and the desire of the occupant to defecate compared to the case where the behavior of the vehicle is not controlled and (iv) an ease assist for easing at least one of the desire of the occupant to urinate and the desire of the occupant to defecate.

The occupant assist apparatus according to the additional statement 5 is capable of executing the appropriate occupant assist based on at least one of the desire of the occupant to urinate and the desire of the occupant to defecate. Typically, the occupant assist apparatus is capable of executing the occupant assist so that the occupant is allowed to take the restroom break more easily, at least one of the desire to urinate and the desire to defecate that the occupant feels does not increase more and/or at least one of the desire to urinate and the desire to defecate that the occupant feels is eased under the situation where the occupant feels at least one of the desire to urinate and the desire to defecate.

(5-6) Additional Statement 6

The occupant assist apparatus according to the additional statement 6 is the occupant assist apparatus according to the additional statement 5, wherein the second driving route includes a driving route that allows the vehicle to travel so that a vibration of the vehicle is smaller than that of the vehicle traveling along another driving route.

The occupant assist apparatus according to the additional statement 6 is capable of executing the appropriate occupant assist so that at least one of the desire to urinate and the desire to defecate that the occupant feels does not increase more. This is because a stimulation to a sphincter of the occupant when the vibration of the vehicle is relatively small is smaller than the stimulation to the sphincter of the occupant when the vibration of the vehicle is relatively large and thus there is a lower possibility that at least one of the desire to urinate and the desire to defecate increases or there is a higher possibility that at least one of the desire to urinate and the desire to defecate is eased.

(5-7) Additional Statement 7

The occupant assist apparatus according to the additional statement 7 is the occupant assist apparatus according to the additional statement 5 or 6, wherein the behavior assist includes an assist for controlling the behavior of the vehicle to allow the vehicle to travel so that a vibration of the vehicle is smaller than that of the vehicle in the case where the behavior of the vehicle is not controlled.

The occupant assist apparatus according to the additional statement 7 is capable of executing the appropriate occupant assist so that at least one of the desire to urinate and the desire to defecate that the occupant feels does not increase more.

(5-8) Additional Statement 8

The occupant assist apparatus according to the additional statement 8 is the occupant assist apparatus according to any one of the additional statements 5 to 7, wherein the ease assist includes at least one of an assist for easing at least one of the desire of the occupant to urinate and the desire of the occupant to defecate by massaging the occupant compared to the case where the occupant is not massaged and an assist for easing at least one of the desire of the occupant to urinate and the desire of the occupant to defecate by controlling an air conditioning compared to the case where the air conditioning is not controlled.

The occupant assist apparatus according to the additional statement 8 is capable of executing the appropriate occupant assist so that at least one of the desire to urinate and the desire to defecate that the occupant feels does not increase more. This is because there is a relatively high possibility that the massage eases at least one of the desire to urinate and the desire to defecate and there is a relatively high possibility that at least one of the desire to urinate and the desire to defecate is eased when a temperature of a vehicle cabin is controlled properly (for example, it is not too cold).

(5-9) Additional Statement 9

The occupant assist apparatus according to the additional statement 9 is the occupant assist apparatus according to any one of the additional statements 1 to 8, wherein the estimating device is configured to (alternatively, the controller is programmed to) estimate at least one of the desire of the occupant to urinate and the desire of the occupant to defecate before the occupant indicates an intention to feel at least one of the desire to urinate and the desire to defecate (for example, the occupant utters a voice relating to at least one of the desire to urinate and the desire to defecate).

The occupant assist apparatus according to the additional statement 9 is capable of estimating at least one of the desire of the occupant to urinate and the desire of the occupant to defecate at the timing when the occupant does not yet indicate the intention to feel at least one of the desire to urinate and the desire to defecate. Thus, the occupant assist apparatus according to the additional statement 9 is capable of executing the appropriate occupant assist based on the result of estimating the desire to urinate and/or defecate of the occupant who does not yet indicate the intention to feel at least one of the desire to urinate and the desire to defecate (for example, the occupant who does not feel at least one of the desire to urinate and the desire to defecate, the occupant who pretends not to feel at least one of the desire to urinate and the desire to defecate or the occupant who cannot indicate the intention to feel at least one of the desire to urinate and the desire to defecate because of a sense of shame although the occupant really feels at least one of the desire to urinate and the desire to defecate).

(5-10) Additional Statement 10

An occupant assist apparatus according to the additional statement 10 is an occupant assist apparatus having: a receiving device that is configured to receive an occupant information relating to an occupant of a vehicle; an estimating device that is configured to estimate, on the basis of the occupant information, at least one of a desire of the occupant to urinate and a desire of the occupant to defecate before the occupant indicates an intention to feel at least one of the desire to urinate and the desire to defecate; and an executing device that is configured to execute an occupant assist on the basis of a result of an estimation by the estimating device.

Alternatively, an occupant assist apparatus according to the additional statement 10 may be an occupant assist apparatus having a controller, the controller is programmed to: receive an occupant information relating to an occupant of a vehicle; estimate, on the basis of the occupant information, at least one of a desire of the occupant to urinate and a desire of the occupant to defecate before the occupant indicates an intention to feel at least one of the desire to urinate and the desire to defecate; and execute an occupant assist on the basis of an estimated result.

The occupant assist apparatus according to the additional statement 10 is capable of executing the appropriate occupant assist based on the result of estimating the desire to urinate and/or defecate of the occupant who does not yet indicate the intention to feel at least one of the desire to urinate and the desire to defecate. Namely, the occupant assist apparatus according to the additional statement 10 is capable of estimating at least one of the desire of the occupant to urinate and the desire of the occupant to defecate and executing the occupant assist based on the estimated result more appropriately.

(5-11) Additional Statement 11

The occupant assist apparatus according to the additional statement 11 is the occupant assist apparatus according to any one of the additional statements 1 to 10, wherein the estimating device is configured to (alternatively, the controller is programmed to) estimate, on the basis of the occupant information, a level of an intensity (in other words, a strength) of at least one of the desire of the occupant to urinate and the desire of the occupant to defecate.

The occupant assist apparatus according to the additional statement 11 is capable of estimating the level of the intensity (in other words, a strength) of at least one of the desire of the occupant to urinate and the desire of the occupant to defecate (namely, an index value that represents how intense, in other words, how strong) that is already felt by the occupant or is estimated to be felt in the future. Thus, the occupant assist apparatus according to the additional statement 11 is capable of executing the appropriate occupant assist based on the result of estimating the level of the intensity of at least one of the desire to urinate and the desire to defecate. Namely, the occupant assist apparatus according to the additional statement 11 is capable of estimating at least one of the desire of the occupant to urinate and the desire of the occupant to defecate and executing the occupant assist based on the estimated result more appropriately.

(5-12) Additional Statement 12

An occupant assist apparatus according to the additional statement 12 is an occupant assist apparatus having: a receiving device that is configured to receive an occupant information relating to an occupant of a vehicle; an estimating device that is configured to estimate, on the basis of the occupant information, a level of an intensity of at least one of a desire of the occupant to urinate and a desire of the occupant to defecate; and an executing device that is configured to execute an occupant assist on the basis of a result of an estimation by the estimating device.

Alternatively, an occupant assist apparatus according to the additional statement 12 may be an occupant assist apparatus having a controller, the controller is programmed to: receive an occupant information relating to an occupant of a vehicle; estimate, on the basis of the occupant information, a level of an intensity of at least one of a desire of the occupant to urinate and a desire of the occupant to defecate; and execute an occupant assist on the basis of the estimated result.

The occupant assist apparatus according to the additional statement 12 is capable of executing the appropriate occupant assist based on the result of estimating the level of the intensity of at least one of the desire to urinate and the desire to defecate. Namely, the occupant assist apparatus according to the additional statement 12 is capable of estimating at least one of the desire of the occupant to urinate and the desire of the occupant to defecate and executing the occupant assist based on the estimated result more appropriately.

At least one portion of the feature in the above described embodiment may be eliminated or modified accordingly. At least one portion of the feature in the above described embodiments may be combined with another one of the above described embodiments.

This application is based upon and claims the benefit of priority of the prior Japanese Patent Application No. 2018-175698, filed on Sep. 20, 2018, the entire contents of which are incorporated herein by reference. In addition, the entire contents of the above described Patent Literatures 1 and 2 are incorporated herein by reference.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention. An occupant assist apparatus, which involve such changes, are also intended to be within the technical scope of the present invention.

REFERENCE SIGNS LIST 1 vehicle
111 detect apparatus
112 navigation apparatus
113 personal information DB
114 driving assist sensor
115 CAN
12 ECU
121 information receiving unit
122 toilet desire estimating unit
123 assist executing unit
131 display
132 driving unit
133 air conditioning apparatus
134 massage apparatus

The invention claimed is:
1. An occupant assist apparatus that is mounted on a vehicle,
the occupant assist apparatus comprising a controller,
the controller being programmed to:
receive an occupant information relating to an occupant of the vehicle;
estimate, on the basis of the occupant information, at least one of a desire of the occupant to urinate and a desire of the occupant to defecate in a future than a timing when the occupant information is received; and control the vehicle to execute an occupant assist on the basis of an estimated result, wherein the occupant assist includes at least one of (i) a route propose assist for proposing a driving route that allows the vehicle to travel so as not to increase at least one of the desire of the occupant to urinate and the desire of the occupant to defecate than another driving route, (ii) a behavior assist for controlling a behavior of the vehicle so as not to increase at least one of the desire of the occupant to urinate and the desire of the occupant to defecate compared to the case where the behavior of the vehicle is not controlled and (iii) an ease assist for easing at least one of the desire of the occupant to urinate and the desire of the occupant to defecate.

2. The occupant assist apparatus according to claim 1, wherein the controller is programmed to estimate, on the basis of the occupant information, at least one of the desire of the occupant to urinate and the desire of the occupant to defecate in the future than the timing when the occupant information is received before the occupant is conscious of at least one of the desire to urinate and the desire to defecate.

3. The occupant assist apparatus according to claim 1, wherein the occupant information includes at least one of a biological information of the occupant and an action information relating to an action of the occupant.

4. The occupant assist apparatus according to claim 3, wherein the action information includes at least one of a diet history information relating to a history of a diet eaten by the occupant and an excretion history information relating to a history of an excretion of the occupant.

5. The occupant assist apparatus according to claim 1, wherein the driving route includes a driving route that allows the vehicle to travel so that a vibration of the vehicle is smaller than that of the vehicle traveling along another driving route.

6. The occupant assist apparatus according to claim 1, wherein the behavior assist includes an assist for controlling the behavior of the vehicle to allow the vehicle to travel so that a vibration of the vehicle is smaller than that of the vehicle in the case where the behavior of the vehicle is not controlled.

7. The occupant assist apparatus according to claim 1, wherein the ease assist includes at least one of an assist for easing at least one of the desire of the occupant to urinate and the desire of the occupant to defecate by massaging the occupant compared to the case where the occupant is not massaged and an assist for easing at least one of the desire of the occupant to urinate and the desire of the occupant to defecate by controlling an air conditioning compared to the case where the air conditioning is not controlled.

* * * * *